United States Patent
Butt et al.

(10) Patent No.: US 9,901,885 B2
(45) Date of Patent: Feb. 27, 2018

(54) METHOD AND DEVICE FOR TRANSFERRING GAS MOLECULES FROM A GASEOUS MEDIUM INTO A LIQUID MEDIUM OR VICE VERSA

(71) Applicant: Max-Planck-Gesellschaft zur Foerderung der Wissenschaften e.V., Munich (DE)

(72) Inventors: Hans-Juergen Butt, Kreuztal (DE); Doris Vollmer, Mainz (DE); Xu Deng, Mainz (DE); Maxime Paven, Udenheim (DE); Periklis Papadopoulos, Mainz (DE); Lena Mammen, Mainz (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 183 days.

(21) Appl. No.: 14/653,428

(22) PCT Filed: Dec. 18, 2013

(86) PCT No.: PCT/EP2013/003833
§ 371 (c)(1),
(2) Date: Jun. 18, 2015

(87) PCT Pub. No.: WO2014/095058
PCT Pub. Date: Jun. 26, 2014

(65) Prior Publication Data
US 2016/0045875 A1    Feb. 18, 2016

(30) Foreign Application Priority Data
Dec. 18, 2012  (EP) .................................. 12008422

(51) Int. Cl.
*A01N 1/02* (2006.01)
*B01F 3/04* (2006.01)
(Continued)

(52) U.S. Cl.
CPC ........... *B01F 3/04269* (2013.01); *A61M 1/32* (2013.01); *B01D 19/0031* (2013.01);
(Continued)

(58) Field of Classification Search
None
See application file for complete search history.

(56) References Cited

U.S. PATENT DOCUMENTS

| 3,413,095 A | 11/1968 | Bramson |
| 4,666,668 A * | 5/1987 | Lidorenko ............. B01D 69/10 |
| | | 210/321.72 |
| 2003/0064003 A1 | 4/2003 | Takehisa et al. |

FOREIGN PATENT DOCUMENTS

| EP | 2156856 A1 | 2/2010 |
| WO | 2011001036 A1 | 1/2011 |

(Continued)

OTHER PUBLICATIONS

Deng et al., Science 335: 67-70 (2012; published online Dec. 1, 2011).*

(Continued)

*Primary Examiner* — Erin M. Bowers
(74) *Attorney, Agent, or Firm* — Caesar Rivise, PC

(57) ABSTRACT

The present invention relates to methods and devices for exchanging gas molecules between a gaseous medium and a liquid medium which are particularly suited for applications such as blood oxygenation in heart-lung machines and gas scrubbing. The method of the invention comprises the following steps: a) providing a liquid medium having a surface tension in the range of from 0.02 N/m to 0.06 N/m, (Continued)

b) providing a gaseous medium, c) providing a membrane on an interface between the liquid medium and the gaseous medium, wherein the membrane comprises i) a carrier substrate with through-going openings having a mean diameter in the range from 0.2 μm to 200 μm, and ii) a porous superamphiphobic coating layer with openings having a mean diameter in the range from 0.1 μm to 10 μm, which is provided at least on the substrate surface facing the liquid medium, wherein either the liquid medium or the gaseous medium, preferably the gaseous medium, comprises at least one target gas to be transferred and said membrane is permeable for the at least one gas to be transferred and not permeable for the liquid medium due to the super-amphiphobic properties of the membrane surface facing the liquid medium with respect to said liquid medium, d) contacting the gaseous medium with the liquid medium via said super-amphiphobic layer for a sufficient time to enrich the liquid or gaseous target medium with the at least one gas to be transferred.

20 Claims, 7 Drawing Sheets

(51) Int. Cl.
| | | |
|---|---|---|
| A61M 1/32 | (2006.01) | |
| B01D 19/00 | (2006.01) | |
| B01D 53/22 | (2006.01) | |
| B01D 69/02 | (2006.01) | |
| B01D 69/14 | (2006.01) | |
| A61M 1/16 | (2006.01) | |

(52) U.S. Cl.
CPC ......... B01D 53/228 (2013.01); B01D 53/229 (2013.01); B01D 69/02 (2013.01); B01D 69/148 (2013.01); B01F 3/04262 (2013.01); *A61M 1/1698* (2013.01); *B01D 2325/02* (2013.01); *B01D 2325/38* (2013.01); *B01F 2003/04404* (2013.01)

(56) References Cited

FOREIGN PATENT DOCUMENTS

| WO | WO 2011/001036 | * | 1/2011 |
|---|---|---|---|
| WO | WO 2011/001036 A1 | * | 1/2011 |

OTHER PUBLICATIONS

Deng et al., "Candle Soot as a Template for a Transparent Robust Superamphiphobic Coating", Science, vol. 335 No. 6064, pp. 67-70 (2012).

Feng et al., "A Super-Hydrophobic and Super-Oleophilic Coating Mesh Film for the Separation of Oil and Water", Angewandte Chemie International Edition, vol. 43, No. 15, pp. 2012-2014 (2004).

Paven et al., "Super liquid-repellent gas membranes for carbon dioxide capture and heart-lung machines", Nature Communications, 4:2512 | DOI: 10.1038/ncomms3512 (2013).

McHale et al., "Immersed superhydrophobic surfaces: Gas exchange, slip and drag reduction properties." Soft Matter 6.4 (2010): 714-719.

Luis et al. "Recent developments in membrane-based technologies for CO2 capture." Progress in Energy and Combustion Science 38 (2012) 419-448.

* cited by examiner

METHOD AND DEVICE FOR TRANSFERRING GAS MOLECULES FROM A GASEOUS MEDIUM INTO A LIQUID MEDIUM OR VICE VERSA

BACKGROUND OF THE INVENTION

The present invention relates to a method and device for exchanging gas molecules between a gaseous medium and a liquid medium. More specific embodiments of the invention relate to improved methods and devices for gas transfer in applications such as blood oxygenation in heart-lung machines and gas scrubbing.

Vascular and parenchymal heart and lung diseases represent a major disease burden, socioeconomic problem and are frequent cause of death. Their growing incidence associated with the aging population stimulated research activities with respect to better methods of prevention, diagnosis and treatment. These activities also include the development of improved heart-lung machines. Nowadays extracorporal circulation during open heart surgery or lung operation has developed into a routine procedure. In order to supply the body with sufficient oxygen a heart-lung machine takes over the heart's pumping action and the lung's gas exchange function during surgeries.

One vital component of a heart-lung machine is the oxygenator. Blood that would normally return to the heart through the venae cavae, flows to the oxygenator for oxygenation, carbon dioxide removal, temperature regulation and anesthetic exchanges. The oxygenated blood then returns to the patient, typically through the aorta, bypassing the heart and lungs completely. A membrane oxygenator as currently used consists of a gas-permeable membrane, typically made of multilayered membrane sheets of microporous polypropylene, silicone rubber, or thousands of silica, polypropyleneor polyethylene capillaries. To achieve a large gas exchange capacity, gas and blood flow on opposite sides of the membrane, permitting the blood cells to adsorb oxygen molecules directly.

Unfortunately, all synthetic materials display a more or less pronounced incompatibilty with blood. Contact with the artificial surface can induce hemolysis, protein denaturation and platelet and leukocyte damage and thrombosis. In order to reduce the incompatibility, heparin can be added to blood or the components of the blood circuit can be provided with a heparin coating. Heparin, either as a coating or as a blood additive, reduces the damage to the blood during extracoporal circulation and the deposition of fibrin or platelets on the surface of the membrane. Such a deposition greatly reduces the gas exchange rate.

Lately, superhydrophobic surfaces such as superhydrophobic Teflon tubes were tested for their ability to prevent attachment of blood, platelets, and blood components such as proteins under stationary or flow conditions. However, the results were not encouraging. Due to the low interfacial tension of blood ($\gamma=0.047$ N/m), blood easily impales a superhydrophobic surface, resulting in an increased contact area with the substrate.

Porous polymer membranes are also used in various gas scrubbing applications. For example, acidic gases such as $CO_2$, $SO_2$, $SO_3$, and $H_2S$ are extracted from process and waste gases by contacting these gases via a gas-permeable membrane with a liquid medium such as an aqueous solution of amines which is capable to absorb the acidic gases and, thus, to remove the same from the process or waste gases. The gas-exchange capacity of these membranes tends to be impaired by the insufficient chemical long-term resistance of most of the polymeric membranes commercially available and also by a gradual wetting of the membranes which increases the resistance to mass transfer and may decrease the process efficiency dramatically. Other gas scrubbing processes face similar problems or suffer from a low efficiency.

WO 2011/001036 suggests to use superamphiphobic aerogels as selective membranes which can be permeated by vapours and gases but not by a liquid such as water, e.g. in gas extraction from liquids. The aerogels disclosed therein represent bicontinuous materials which are extremely light weight, highly porous and mechanically rather instable. In particular, their superamphiphobic properties, repellency of both water and oils, cannot be maintained if the aerogel is subjected to a mechanical force such as a hydrostatic pressure, in particular a pressure above about 1000 Pa.

In view of the drawbacks of the prior art, the main object of the present invention was to provide improved methods and devices for transferring gas molecules from a gaseous medium into a liquid medium of low surface tension or vice versa, in particular in applications such as blood oxygenation in heart-lung machines, and gas scrubbing.

This objective has been achieved by providing the novel methods for gas transfer and the devices according to the invention.

DESCRIPTION OF THE INVENTION

The method for transferring gas molecules from a gaseous medium into a liquid medium or vice versa according to the present invention comprises at least the following steps:
a) providing a liquid medium having a surface tension (liquid-air) in the range of from 0.02 N/m to 0.06 N/m,
b) providing a gaseous medium,
c) providing a membrane on an interface between the liquid medium and the gaseous medium, wherein the membrane comprises
i) a carrier substrate with through-going openings having a mean diameter in the range from 0.2 µm to 200 µm, preferably in the range from 1 µm to 50 µm, and
ii) a porous superamphiphobic coating layer with openings having a mean diameter in the range from 0.1 µm to 10 µm, which coating layer comprises a surface exhibiting an apparent, macroscopic contact angle of at least 150° with respect to 10 µl sized drops of water and also an apparent, macroscopic contact angle of at least 150° with respect to 10 µl sized drops of liquids having a surface tension of not more than 0.06 N/m, in particular oils, alkanes, and aromatic compounds, which is provided at least on the substrate surface facing the liquid medium,
wherein either the liquid or the gaseous medium, preferably the gaseous medium, comprises at least one target gas to be transferred and said membrane is permeable for the at least one gas to be transferred and not permeable for the liquid medium due to the superamphiphobic properties of the membrane surface facing the liquid medium with respect to said liquid medium,
d) contacting the gaseous medium with the liquid medium via said superamphiphobic layer for a sufficient time to enrich the liquid or gaseous target medium with the at least one gas to be transferred.

The target gas to be transferred is not especially limited and may be any gas which is desired to transfer from a gaseous into a liquid medium or vice versa. In more specific embodiments, the target gas is selected from the group comprising oxygen, carbon dioxide, $H_2S$, HCl, HCN, $TiCl_4$, nitrogen oxides, ammonia and amines, silanes, such as tetraethoxysilane (TEOS) or hexamethyldisiloxane (HMDSO).

A second, closely related aspect of the invention pertains to a device for transferring gas molecules from a gaseous medium into a liquid medium or vice versa comprising:
a) a liquid medium having a surface tension (liquid-air) in the range of from 0.02 N/m to 0.06 N/m,
b) a gaseous medium,
c) a membrane provided on an interface between the liquid medium and the gaseous medium, wherein the membrane comprises
i) a carrier substrate with through-going openings having a mean diameter in the range from 0.2 µm to 200 µm, preferably in the range from 1 µm to 50 µm, and
ii) a porous superamphiphobic coating layer with openings having a mean diameter in the range from 0.1 µm to 10 µm, which coating layer comprises a surface exhibiting a contact angle of at least 150° with respect to 10 µl sized drops of water and also a contact angle of at least 150° with respect to 10 µl sized drops of liquids having a surface tension of not more than 0.06 N/m, in particular oils, alkanes, and aromatic compounds, which is provided at least on the substrate surface facing the liquid medium,
which membrane is permeable for the at least one gas to be transferred, preferably comprised in said gaseous medium, and not permeable for the liquid medium due to the superamphiphobic properties of the membrane surface facing the liquid medium with respect to said liquid medium.

The liquid medium and the gaseous medium in said device may be contained in different compartments, wherein at least one partition between the liquid medium and the gaseous medium is provided and which partition is constituted by a super-amphiphobic membrane as defined herein.

In one specific embodiment, said superamphiphobic membrane comprises or consists of a porous 3-dimensional structure with a defined shape and either the liquid medium or the gaseous medium is contained therein.

More specifically, said superamphiphobic membrane comprises or consists of an elongated tubular body having a rounded or rectangular cross-section, such as a capillary, or any other longitudinally or 2-dimensionally extended hollow body having at least one lumen or cavity provided in the interior thereof and either the liquid medium or the gaseous medium is contained in said lumen or cavity or passes through the same. The superamphiphobic membrane may also, for example, have a similar form as conventional gas-permeable membranes of the art.

The device may further contain means for moving either the liquid medium or the gaseous medium or both relatively to one another and/or to the membrane. Such a movement may be effected discontinuously or continuously, e.g. a steady flow, with a continuous movement generally being preferred.

In preferred embodiments of the invention, this device is a gas scrubber or the oxygenator of a heart-lung machine or a component thereof.

A further closely related aspect of the invention pertains to the use of the above methods and/or devices in various applications involving the exchange, enrichment or purification of gases. Specific applications of interest are for example in the fields of gas scrubbing, in particular amine wash, flue gas desulfurization, silane capturing, and in the field of medicine, in particular for oxygenation of blood.

A major benefit of the present invention resides in the fact that the membrane comprising a carrier substrate with rather large through-going openings having a mean diameter in the range from 0.2 µm to 200 µm, preferably in the range from 0.3 µm to 150 µm, more preferred 1 µm to 100 µm, such as 1 µm to 50 µm, and having the superamphiphobic coating layer provided on at least one surface of the substrate enables an effective selective gas transfer even into or from liquid media of a very low surface tension such as 0.02 N/m or 0.03 N/m.

These large through-going openings provide a large specific area available for gas exchange and, thus, considerably enhance the efficiency of the gas transfer. Gas exchange membranes of the prior art (without a superamphiphobic coating layer) typically exhibit only relatively small openings/pores in the range of below 1 µm, usually below 0.2 µm or 0.1 µm, in order to avoid membrane wetting and permeating of liquid through the membrane.

The presence of the superamphiphobic coating layer effectively prevents wetting of the membrane used in the method or device of the invention even in the presence of a liquid with low surface tension and, consequently, also prevents permeating of the liquid through said membrane. Such superamphiphobic membranes are able to provide a very high effective porosity of close to 100% which results in a highly efficient gas transfer/exchange.

The term "superamphiphobicity" as used herein generally means an extremely low affinity or extremely high repellency for water as well as for liquids of low surface tension such as oils, alkanes etc. A superamphiphobic surface typically exhibits an apparent advancing contact angle of at least 150° with respect to 10 µl sized drops of water and also an apparent advancing contact angle of at least 150° with respect to 10 µl sized drops of liquids having a surface tension of not more than 0.06 N/m, in particular oils, alkanes, aromatic compounds, and also aqueous solutions comprising a surface tension reducing agent.

The apparent advancing contact angle is the macroscopically observed contact angle (such as observed with the naked eye or a low resolution microscope). It relates to a length scale much larger than the nano- or microstructures forming the superamphiphobic layer, thus to a length scale typically larger than 1 µm, in particular larger than 100 µm.

A superamphiphobic surface typically also exhibits a sliding or roll off angle below 10° or even below 5° for water, blood, surfactant solutions, aqueous solutions and most organic liquids, in particular oils, alkanes, aromatic compounds.

A droplet deposited on a superamphiphobic surface rolls off easily, leaving the surface dry and clean. This remarkable property is due to a surface structure which favours the entrainment of air cushions beneath the drop leading to the so called Cassie state. The Cassie state competes with the Wenzel state where the liquid fully wets the substrate. To generate a superamphiphobic surface, 3 key features are required: a low surface energy of the material, a topography with roughness on the nano- and microscale, and the presence of overhang structures. In this case, air (or another gas present) can be entrained when placing a sessile drop on top, which leads to the low adhesion.

Methods for generating such superamphiphobic surfaces are known in the art and some preferred methods resulting in superamphiphobic surfaces with especially favourable characteristics are described below.

The material or shape of the carrier substrate with through-going openings having a mean diameter in the range from 0.2 µm to 200 µm, preferably in the range from 1 µm to 50 µm, is not especially limited.

In specific, non-limiting embodiments the carrier substrate comprises or consists of a mesh, preferably a metal mesh, fibers, a textile, a micro- or mesoporous foam or a porous 3-dimensional structure with a defined shape, e.g. a porous capillary, or combinations of those.

More specifically, said porous 3-dimensional structure with a defined shape comprises an elongated tubular body having a rounded or rectangular cross-section or any other longitudinally or 2-dimensionally extended hollow bodies having at least one lumen or cavity provided in the interior thereof.

In one specific embodiment of the method or device of the invention, the liquid medium is provided in at least one lumen or cavity in the interior of a porous 3-dimensional membrane structure and the gaseous medium is provided on the exterior of said structure, or vice versa.

In another specific embodiment of the method or device of the invention, the membrane comprises a carrier substrate with a microporous or mesoporous superamphiphobic layer provided on at least one substrate surface and said porous layer is partially filled with the gaseous medium. Preferably, said porous layer does not comprise or consist of an aerogel, i.e. a highly porous solid formed from a solvent swollen network gel, in which the liquid is replaced with a gas, in particular not an aerogel as disclosed in WO 2011/001036 cited above.

A further benefit of the present invention results from the fact that the superamphiphobic membrane used is mechanically stable and does not loose its superamphiphobic properties even if a mechanical force such as a hydrostatic pressure is applied. The method or device of the invention is suitable for working conditions where the liquid medium exerts a hydrostatic pressure of at least 100 Pa, typically at least 500 Pa or 1000 Pa, or even at least 5 kPa or 10 kPa (in particular for aqueous solutions), onto the superamphiphobic layer of the membrane.

The superamphiphobic layer of the membrane used in the method and device of the present invention preferably comprises strings, particles embedded in fibers, columns, aggregates or a fractal-like arrangement of smooth or rough nano- or microparticles having a mean diameter in the range of 12 nm to 2 µm, preferably 20 nm to 2 µm, more preferred 20 nm to 1 µm, in particular 20 nm to 100 nm or 40 nm to 200 nm, which particles either consist of a material of low energy surface or are coated with a material of low surface energy, wherein the low surface energy material is characterized in that the surface tension (air-substrate surface) is less than 0.03 N/m, preferably below 0.02 N/m.

Said strings, columns, aggregates or fractal-like arrangement of nano- or microparticles may form an interconnected network, however, preferably the strings, columns and aggregates of nano- or microparticles do not form such an interconnected network and the topmost part of the coating consists of essentially isolated strings, columns and aggregates of nano- or microparticles.

Further, the superamphiphobic coating layer may be provided on one or more surfaces of the carrier substrate. In a preferred embodiment wherein the carrier is a mesh, the coating layer is not only present on the top (and/or bottom) surface of the mesh but also present in the space between the mesh openings. In an especially preferred embodiment, the superamphiphobic coating layer essentially spans the entire mesh openings.

The superamphiphobic coating layer has a mean thickness between 0.4 µm and 500 µm, preferably between 1 µm and 100 µm, more preferred between 3 µm and 50 µm.

The membrane comprising such a superamphiphobic coating layer can be obtained by providing a carrier substrate with through-going openings having a mean diameter in the range from 0.2 µm to 200 µm, preferably in the range from 1 µm to 50 µm, depositing particles having a mean diameter in the range of from 12 nm to 2 µm, preferably 20 nm to 2 µm, more preferred 20 nm to 1 µm, on the substrate surface, e.g. by spray coating, electrospinning, sedimentation or by growing the particles on the carrier substrate, and, optionally, coating the particles with a hydrophobic top coating.

These particles may be, e.g., polymer particles (polystyrene, polymethymethacrylate) or composite particles, PTFE, silica particles, e.g. Aerosil, or particles coated with a shell, which shell may be a silica shell, a shell of a material such as $AlO_2$, $CeO_2$, $SnO_2$, $TiO_2$, or other metal oxides, $Ti\{OCH(CH_3)_2\}_4$, or a hybrid shell comprising 2 or more materials, in particular selected from the above. Also, polymer lattices may be coated with a silica, metal oxide or other shell. The silica particles or particles or polymer lattices coated with a (silica or other) shell are further coated with a hydrophobic top coating, such as PDMS, semi-fluorinated silanes or semi-fluorinated polymers, or mixtures containing these components.

Optionally, the particles, strings, fibers, columns or aggregates may be functionalized and/or crosslinked with a suitable agent, such as a crosslinking polymer. In a more specific embodiment, the crosslinking polymer may be a fluorinated or perfluorinated polymer, such as poly-3-(trimethoxysilyl) propylmethacrylate-co-1H,1H-perfluorooctyl methacrylate, which allows a simultaneous crosslinking and hydrophobization.

In one preferred embodiment of the invention, the membrane is produced by coating a carrier substrate with through-going openings having a mean diameter in the range from 0.2 µm to 200 µm, preferably in the range from 1 µm to 50 µm, with soot particles having a mean diameter in the range of from 12 nm to 100 nm, preferably 20 nm to 80 nm, coating the soot particles with a silica shell, e.g. by the Stöber method, calcinating the particles and coating the calcinated particles with a hydrophobic coating. This method corresponds to an analogous method for producing a superamphiphobic coating on a glass substrate developed by the present inventors and described in *Science* 335, 67 (January 2012) and Nature Communications 4:2512 doi: 10.1038/ncomms3512 (2013).

In another preferred embodiment of the invention, the membrane is produced by providing a carrier substrate with through-going openings having a mean diameter in the range from 0.2 µm to 200 µm, and growing silica particles on the substrate surface following the Stöber method, that is formation of silica by hydrolysis and condensation of tetraethoxysilane (TES) or other organic silanes catalyzed by ammonia. Silica particles also grow in solution. These particles sediment. Remaining TES in solution chemically binds neighbouring sedimented particle, sedimented particles to particles grown on the surface and binds the particle to the surface. In the course of this process, the substrate surface becomes decorated with silica particles. The size of the silica particles can be adjusted by varying the reaction parameters such as the amount of silane.

The gaseous medium used in the method or device of the invention is not especially limited and may be any gaseous medium containing gas molecules desired to remove, preferably selectively, therefrom or any gaseous medium desired to be enriched with gas molecules of a target gas. Preferably, the gas molecules are molecules of a target gas as defined above, in particular selected from the group comprising oxygen, carbon dioxide, $H_2S$, HCl, HCN, $TiCl_4$, nitrogen oxides, ammonia and amines, silanes, such as tetraethoxysilane (TES) or hexamethyldisiloxane (HMDSO).

In a specific embodiment, the gaseous medium is selected from the group comprising oxygen, air or another oxygen containing mixture of gases, natural gas, a process gas or an industrial waste gas.

The liquid medium used in the method or device of the invention is not especially limited as long as its surface tension is in the range of from 0.02 N/m to 0.06 N/m, in particular in the range from 0.03 N/m to 0.055 N/m or 0.04 N/m to 0.05 N/m.

More specifically, the liquid medium is selected from the group comprising aqueous media, including blood and aqueous solutions of components capable to reduce the surface tension of water to 0.06 N/m or below, preferably selected from the group comprising amines, such as ethanolamine, diethanolamine, methyldiethanolamine, diisopropylamine, diisopropanolamine, diglycolamine, surfactants, lipids, peptides, proteins, polyelectrolytes, DNA, polymers, block copolymers, silanes, and functionalized particles, lime water, organic media comprising organic solvents such as alkanes, alcohols, aromatic compounds and optionally further components, ionic liquids, and mixtures thereof.

In particular, the ionic liquid may be selected from the group of ionic liquids based on organic cations such as imidazolium, pyridininum, pyrrolidinium, guanidinium, uronium, thiouronium, piperidinium, morpholinium, ammonium or phosphonium cations and organic or inorganic anions such as, e.g. halogenides, tetrafluoroborates, trifluoracetates, phosphinates, tosylates, imides (such as bis(trifluoromethylsulfonyl)imide ($Tf_2N^-$) and amides. More specifically, the ionic liquid is selected from ionic liquids based on imidazolium cations such as 1-n-butyl-3-methylimidazolium (bmim), 1-butyl-3-methylpyridinium (bmpy), 1,2-dimethyl-3-propyl-imidazolium (pmmim) and 1-methyl-3-(3,3,4,4,5,5,6,6-octafluorohexyl)imidazolium (F-hmim) and organic anions such as bis(trifluoromethylsulfonyl)imide. The ionic liquids may also be polyionic liquids obtained by polymerization of ionic monomers (e.g. as mentioned above). Further, ionic liquids may be used in combination with other solvents such as alcohols, e.g. PEG.

Generally, the liquid medium used in the method or device of the invention will be selected such that it is capable to effectively absorb or bind gas molecules of a given target gas from a gaseous medium. Thus, depending from the intended application of said method or device, specific combinations of gaseous medium and liquid medium will be used.

If, for example, in the fields of gas scrubbing an acidic gas is to be removed from a gaseous medium, such as a process gas or waste gas, the liquid medium is preferably a (typically basic) medium capable to bind, absorb or neutralize said acidic target gas, e.g. carbon dioxide, $SO_2$, $SO_3$, $H_2S$, HCN etc. In this case, the liquid medium may, e.g., contain amines, such as ethanolamine, diethanolamine, methyldiethanolamine, diisopropylamine, diisopropanolamine, diglycolamine ("amine wash") or other basic compounds such as carbonate/bicarbonate.

Also, ionic liquids, in particular such as mentioned above, may be effectively used for carbon dioxide capturing. For flue gas contaminants such as $SO_2$, $SO_3$ etc. the liquid medium may be lime water or any other basic medium known in the art of flue gas desulfurization.

Similarly, basic gases such as ammonia can be effectively removed from a gaseous medium by the use of an acidic liquid medium.

Suitable liquid media for silane capturing are for example aqueous solutions.

In one preferred embodiment of the invention, the liquid medium comprises or consists of blood, the gaseous medium is oxygen or an oxygen-containing gas mixture and the at least one gas to be transferred from the gaseous medium is oxygen. Thus, the method or device of the invention can be advantageously used for blood oxygenation.

In a related aspect, the liquid medium comprises or consists of blood, the gaseous medium is oxygen or an oxygen-containing gas mixture and the at least one gas to be transferred from the liquid medium is carbon dioxide. Thus, the method or device of the invention can be advantageously used for blood "reactivation".

1A: gas transfer through a capillary (length 3 cm, diameter 3 mm) formed from a metal mesh-based membrane: UV-VIS spectrum as a function of wavelength 1B: gas transfer through a flow cell with 2 flat membranes based on a metal mesh (mesh width 0.032 mm): UV-VIS spectrum as a function of time at the constant wavelength of 555 nm (absorption maximum of phenolphthalein)

FIG. 2 UV-VIS spectra of oxygenated and deoxygenated blood (1.2%) in PBS

2A: Oxygenation by oxygen diffusion through a superamphiphobic membrane recorded in a flow cell.

2B: control

Figure 3A:
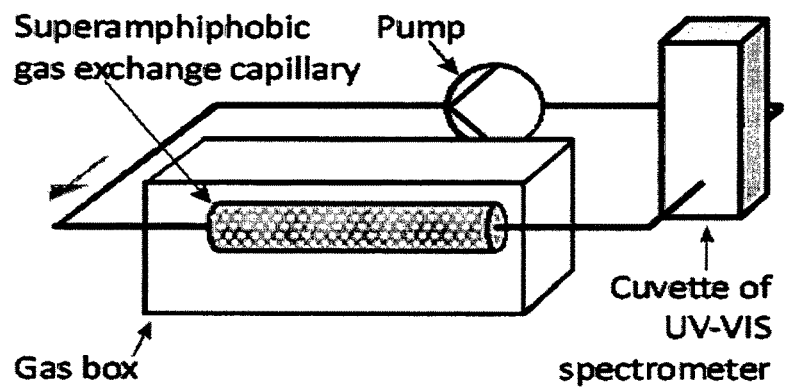

FIG. 3 Experimental setups

3A: Scheme of the principal setup for effecting and monitoring gas transfer through a superamphiphobic membrane including pump, cuvette, gas chamber, capillary/flow cell Not shown: gas reservoir.

3B: Scheme of a flow cell with two mountable superamphiphobic membranes

3C: Photographs of superamphiphobic capillaries using a metal mesh as carrier substrate FIG. 4 shows the relative adsorption of blood proteins and blood cells to different surfaces including a superamphiphobic surface.

4A: quantitative protein adsorption (Pierce test)

4B: SEM micrographs showing adsorption of blood to an uncoated metal mesh (left) versus a superamphiphobic mesh (right)

FIG. 5 shows TEM micrographs of particles constituting the superamphiphobic layer of the membrane used in the invention 5A: Fractal network formed by soot particles imaged by scanning electron microscopy (SEM)

5B: String of soot particles (SEM image)

5C: Soot particles after coating with a silica shell (SEM image)

5D: High magnification image of soot particles after coating with a silica shell (SEM image)

5E: Transmission electron microscope image of coating after calcination showing the silica shell FIG. 6 shows strings and fibers comprising particles with a silica shell and PVA (SEM micrographs)

6A: Strings composed of PVA and silica particles of 1000 nm diameter

6B: Fiber composed of PVA and silica particles of 200 nm diameter

The following non-limiting examples are provided to illustrate the present invention in more detail, however, without limiting the same to the specific features and parameters thereof.

Example 1

Preparation of a Superamphiphobic Layer on a Mesh

Figure 5A:
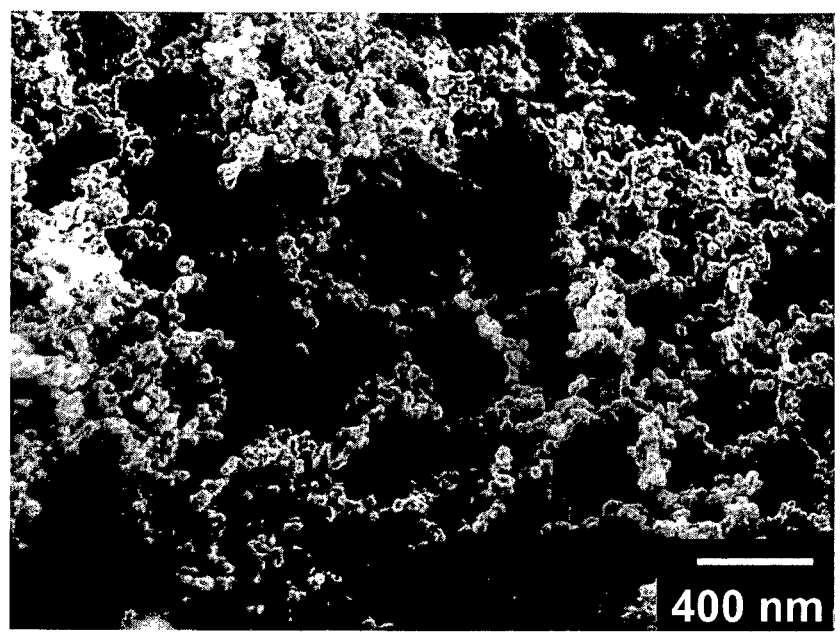
Figure 5B:
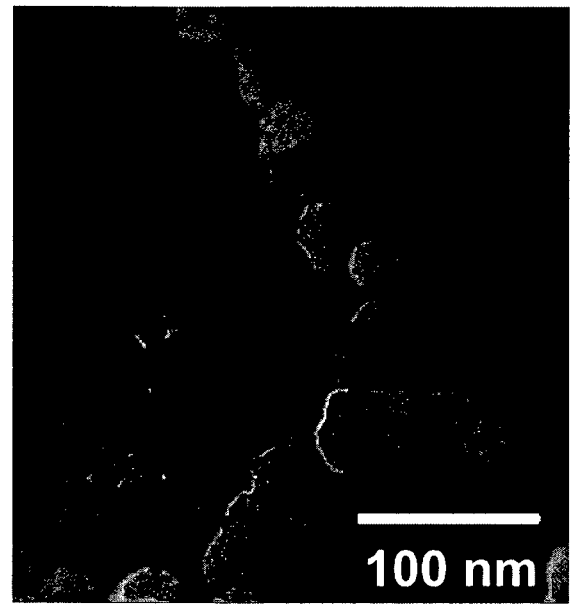
Figure 5C:
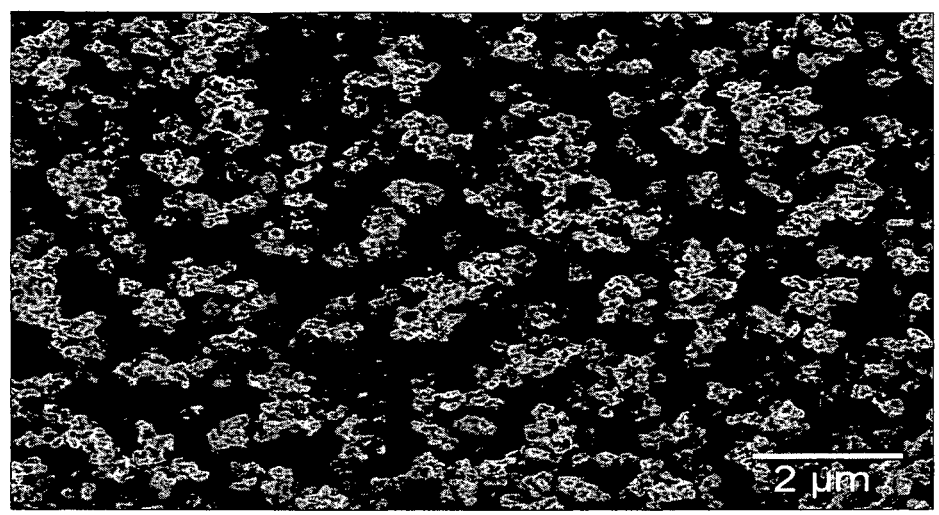
Figure 5D:
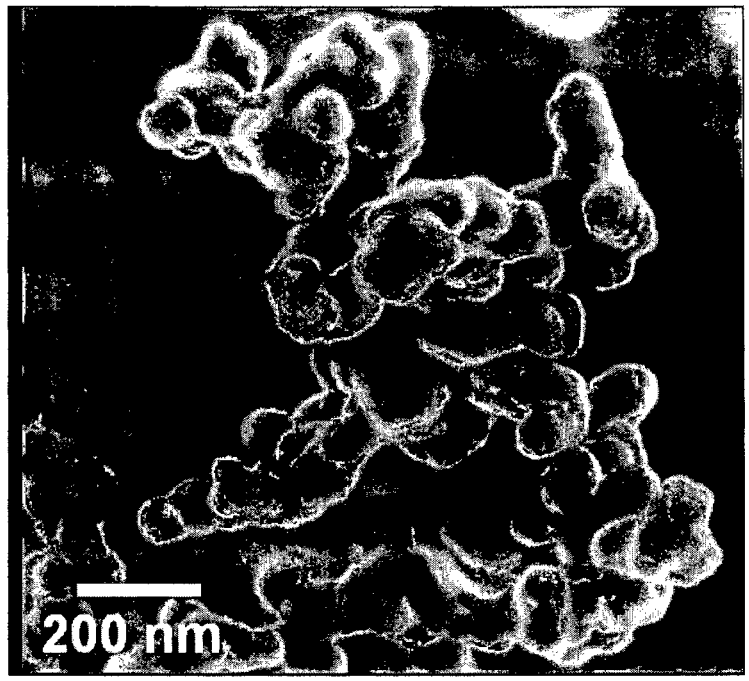
Figure 5E:
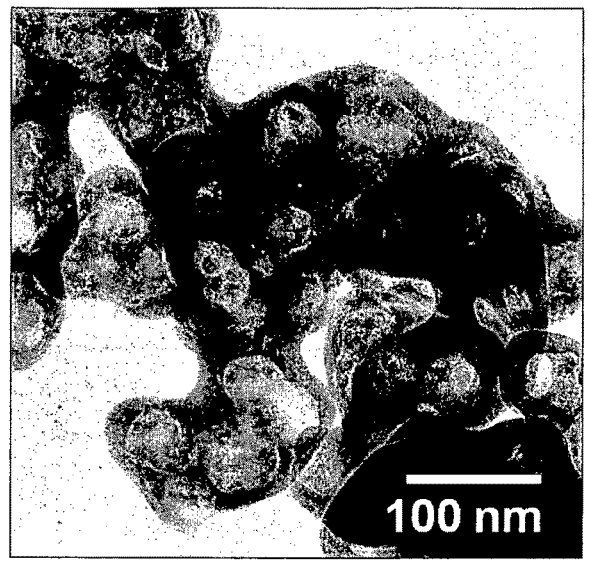

The surface to be coated, in this case a metal mesh, was held above a flame of a paraffin candle. Deposition of a soot layer immediately turned the metal black. Scanning electron microscopy revealed that the soot consists of carbon particles with a typical diameter of 30-40 nm, forming a loose, fractal-like network (FIG. 5B). A water drop gently deposited on the surface shows a contact angle above 160° and rolls off easily, proving the surface's superhydrophobicity. However, the structure is fragile as the particle-particle interactions are only physical and weak. When water rolls off the surface, the drop carries soot particles with it until almost all of the soot deposit is removed and the drop undergoes a wetting transition. Therefore, in order to stabilize this structure the soot layer is coated with a silica shell making use of chemical vapour deposition (CVD) of tetraethoxysilane (TES) catalyzed by ammonia. The soot-coated substrates were placed in a desiccator together with two open glass vessels containing tetraethoxysilane (TES) and ammonia, respectively. Similar to a Stöber reaction, silica is formed by hydrolysis and condensation of TES. The shell thickness can be tuned by the duration of CVD. After 24 h the particles are coated by a 20±5 nm thick silica shell (FIG. 5C, D). Calcinating the hybrid carbon/silica network at 600° C. for 2 h in air causes combustion of the carbon core (FIG. 5E) and a decrease in the shell thickness, while the layer keeps its roughness and network texture. Only isolated chains of particles, which are not linked in the network, broke during calcination. To reduce the surface energy the hydrophilic silica shells were coated by a semi-fluorinated silane by chemical vapor deposition. After fluorination a water drop placed on top of the coating formed a static contact angle of 165°±1°, with a roll-off angle lower than 1°. Owing to the extremely low adhesion of the coating, with water it was difficult to deposit water drop, because they immediately tended to roll off. When drops of organic liquid were deposited, the static contact angles ranged from 154° for tetradecane up to 162° for diiodomethane.

FIG. 6 shows strings and fibers comprising particles with a silica shell and PVA (SEM micrographs) obtained by mixing an aqueous dispersion of PVA and silica colloids.

Figure 6A:
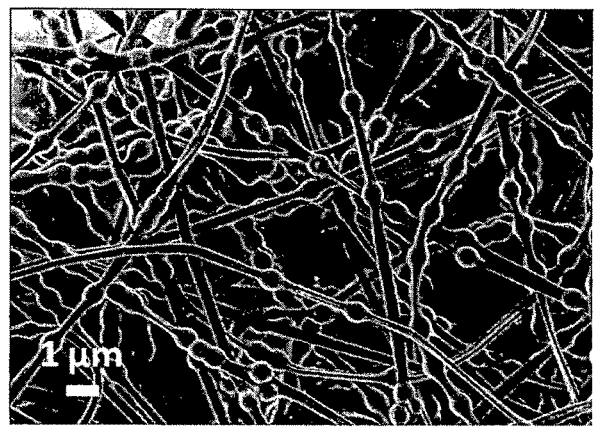

Stirring of 10 wt % PVA for 3 h at 85° C. and subsequently adding 56 wt % silica particles (1000 nm) resulted in a network comprising necklace-like strings (shown in FIG. 6A). The final concentrations of silica, PVA and water were 8 wt %, 8 wt % and 84 wt %, respectively.

Figure 6B:
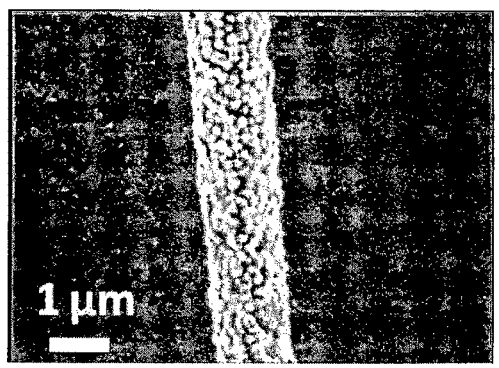

Stirring of 10 wt % PVA for 3 h at 85° C. and subsequently adding 32 wt % silica particles (200 nm) resulted in a fiber structure (shown in FIG. 6B). The final concentrations of silica, PVA and water were 8 wt %, 8 wt % and 84 wt %, respectively.

These strings and fibers can be immobilized on a desired carrier substrate surface by contacting the above or similar mixtures with the carrier substrate using any suitable method of the art, e.g. by means of electrospinning.

Example 2

Oxygenation of Blood Via a Superamphiphobic Membrane

Figure 3B:
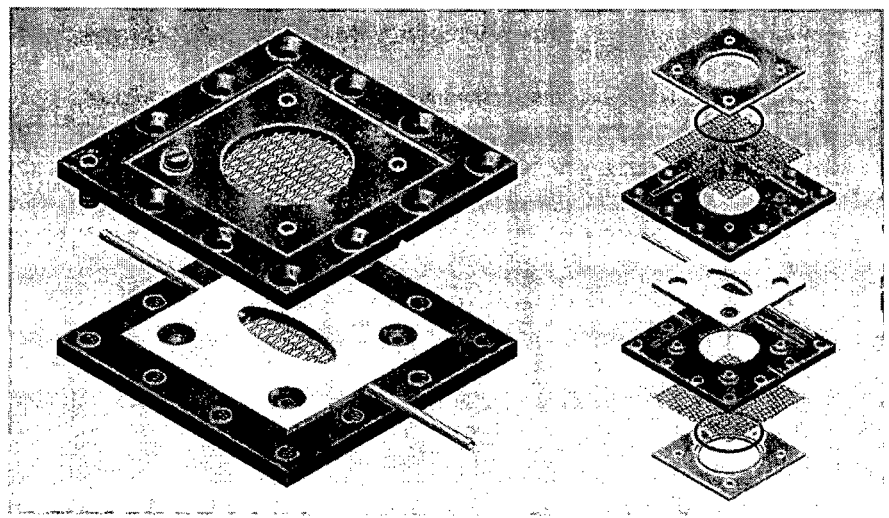
Figure 3C:
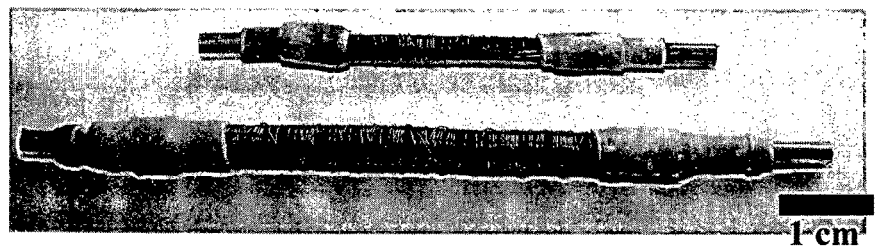

The controlled oxygenation of deoxygenated blood by oxygen diffusion through a superamphiphobic membrane in a closed pumped system was shown to be possible using a flow cell with two superamphiphobic membranes as side walls (FIG. 3B). Depending on the specific application superamphiphobic meshes of different sizes can be prepared separately and then be fixed in the flow cell. It is also possible to place two meshes right behind another if desired.

The cell was placed into an air tight gas box. This gas box was equipped with two valves for in-flowing and out-flowing gas, connection tubes for in-flowing and out-flowing liquid and an oxygen partial pressure sensor.

For these experiments, stainless steel meshes with a mesh-width of 32 micrometer and a wire diameter of 28 micrometer were used. The surfaces were made superamphiphobic using the procedure described in Example 1. The inner compartment of the flow cell has an elliptical flow profile with a transverse diameter of 2 cm, a conjugate diameter of 1 cm and a depth of 2 mm between the two superamphiphobic mesh-walls, resulting in an entire volume of 3.1 cm². The inner diameter of the cell influx and out-flux tube is 1.37 mm. The flow cell was connected to a tubing pump (flow=4 ml/min), a reservoir and a UV-VIS flow cuvette using Tygon® tubing (inner diameter=1.42 mm). FIG. 3A shows the principal experimental setup including pump, cuvette, gas chamber, capillary/flow cell (note that a capillary of a desired alternate shape, e.g. such as described in Example 3, could also be used instead of the flow cell as described above).

The gas box was flushed with a constant $N_2$ stream for 2 hours, until no more oxygen could be detected by the oxygen partial pressure sensor. Deoxygenated 1.2% blood/PBS solution (see above) was transferred to the reservoir under inert gas conditions. The total volume of the entire system was approx. 19 ml. Spectra were measured subsequently; the measurement of one spectrum took approximately 1 min 17 sec.

Figure 2A:
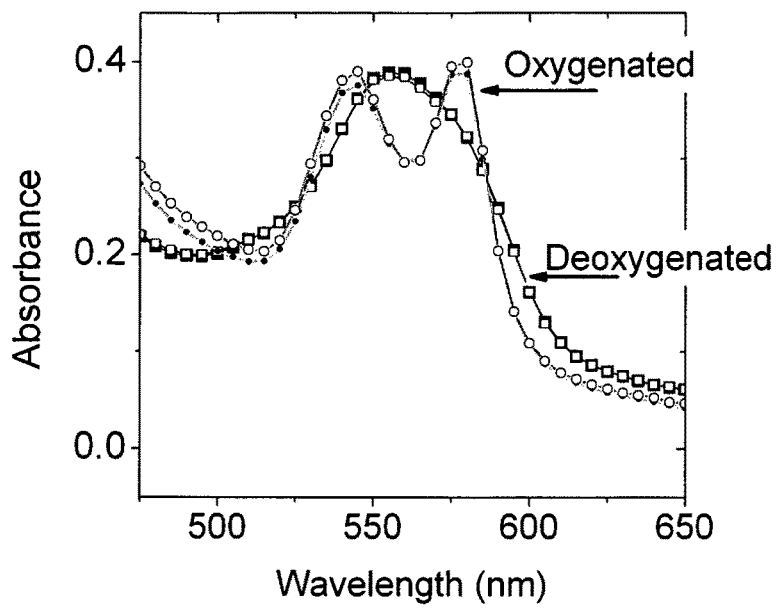

The gas box was flushed for further 16 min with $N_2$ and then subsequently flushed with 5 balloons (V=3-4 liter) of oxygen over a period of 29 min. The spectrums for t=0 min and t=45 min are shown in FIG. 2a. Comparison of FIG. 2a with FIG. 2B (control) demonstrates that pumped blood/PBS was successfully oxygenated. The solution was pumped for more than 1 hour in a closed system without any leakage.

Figure 2B:
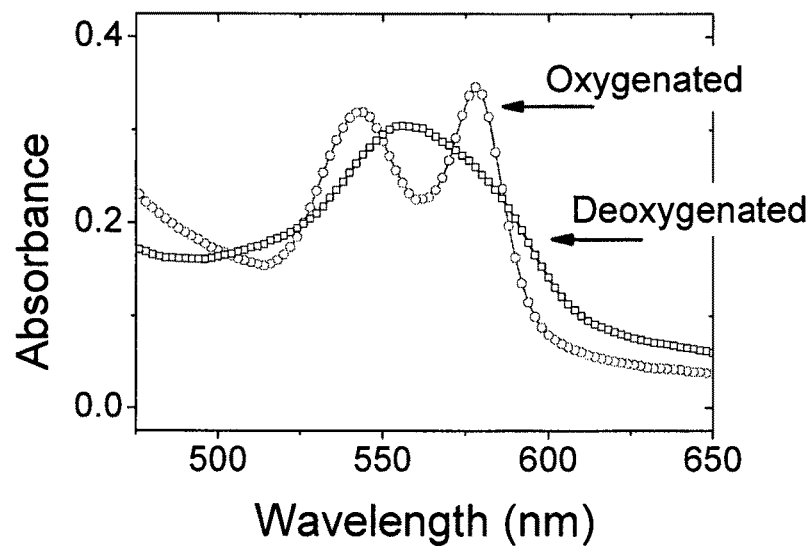

The timescale of oxygenation depends on various points:
Size of gas box (V=~2 liter)
Flushing speed/time needed for replacement of $N_2$ by $O_2$ atmosphere
Total Area of interfacial membrane (A=3.1 cm²)
Mesh width
Flow speed of the liquid Direct oxygenation of blood was conducted and measured in a control experiment as follows:

UV-VIS-spectra of oxygenated and deoxygenated blood were measured in a sealed cuevette (d=2 mm) (FIG. 2B).

1.2% blood in PBS solution was oxygenated under ambient conditions. For this, the 20 ml Hellma cuvette was kept open for 20 min and the blood was slightly stirred. The oxygenized blood was directly measured. In order to deoxygenize the blood/PBS solution, the solution was heated to 37° C. and a continuous stream of $N_2$ was bubbled through the liquid over 30 min. The blood/PBS solution was then transferred to a sealable cuevette under inert-gas conditions and the sample was measured as well. Spectra are baseline corrected to 800 nm (isosbestic point of hemoglobin).

Example 3

Gas Diffusion Through a Superamphiphobic Membrane

Experimental Setup:

The same principal setup as described in Example 2 for the oxygenation of blood/PBS solutions was used. Again, it consisted of a pump, Tygon®-tubing, a flow cuvette, a reservoir and an air-tight gas box containing a superamphiphobic capillary/flow cell. The gas box was equipped with two valves for in-flowing and out-flowing gas, connection tubes for in-flowing and out-flowing liquid and an oxygen partial pressure sensor. In this case, sodium hydroxide solution with phenolphthalein was pumped through the capillary or flow cell. The capillary and the flow cell both partly consist of a superamphiphobic mesh, which was coated as described in Example 1 by deposition of paraffin candle soot, CVD of tetraethoxysilane and hydrophobization with trichlorofluorosilane. These meshes act as membranes and form a barrier to the outer gas atmosphere. The gas box was either filled with $N_2$ or $CO_2$.

The flow cell used was similar to or identical with the flow cell in Example 2. For the gas diffusion experiments described herein, superamphiphobic capillaries (FIG. 3C) were also used. The manufacturing of these capillaries was slightly different from the manufacturing of plane superamphiphobic surfaces. A mesh piece with the size of about 3 cm to 6 cm×1 cm is covered for ~45 s with candle soot from one side. Afterwards the soot template is stabilized by chemical vapor deposition of tetraethoxysilane for 24 h in a desiccator (in analogy to the usual procedure). The samples were calcinated at 600° C. for 2 hours. After calcination the meshes were shaped into capillaries by hand. The inner part of the tube was coated with the fractal silica network; the outer part of the tube had no coating. The capillaries had an inner diameter of ~2.5 mm to 3 mm and a length of 3 cm to 6 cm. These capillaries were permanently fixed by wrapping a copper wire (d=0.01 mm) around them. The average distance between neighboring copper strings was 1 mm to 2 mm. These capillaries were hydrophobized. For this, 300 microliter semifluorinated trichlorosilane was put in an open glass vessel and placed in a desiccator for 2 hours at ~200 mbar (in analogy to the standard procedure described in Example 1). In order to connect the superamphiphobic capillaries with the pump system stainless steel metal tubes with a length of 1.3 cm and an inner diameter of 2 mm were fixed at the opening of the superamphiphobic capillaries with the help of heat-shrink tubes. To make a tight connection between the capillary and the metal tube, one shrinking tube of length=1 cm and an inner diameter=0.6 cm was placed first from each side and heated. An equal piece was put over the one beforehand with an offset of ~0.5 cm, so that one half of the prior shrinking tube was covered and one half of the superamphiphobic capillary was covered (see capillary at top, FIG. 3C). In some cases, a third piece of shrinking tube with length=~0.5 cm and an inner diameter=0.3 cm was placed over the connection part between metal tube and first shrinking tube and was heated (see capillary at bottom, FIG. 3C). Shrinking tubes were heated using a fire-lighter.

To prove that gas can diffuse through these superamphiphobic meshes, the acid-base neutralization of sodium hydroxide with carbonic acid was used as a model system. Therefore, in a first step a sodium hydroxide solution with phenolphthalein as indicator was prepared. Phenolphthalein is pink in the presence of base and turns colorless in the neutral and acidic regime ($pK_s$=9.7). The tubing system and the gas box containing the superamphiphobic capillary or flow cell were flushed 7 times with 3-4 liter $N_2$. The basic phenolphthalein solution (pink) was transferred to the reservoir (total volume of approx. 19-22 ml). After a predetermined time (about 25 min) the gas box was flushed with $CO_2$. If the superamphiphobic meshes are permeable to gas, $CO_2$ will have contact to the pumped solution after a certain diffusion time. The pumped solution mainly consists of water and in the presence of water $CO_2$ is in equilibrium with carbonic acid (Equation 1). The carbonic acid will be neutralized by the dissolved sodium hydroxide. Once all sodium hydroxide is neutralized, phenolphthalein will turn colorless and the solution loses its characteristic UV-VIS absorption bands.

Figure 1A:
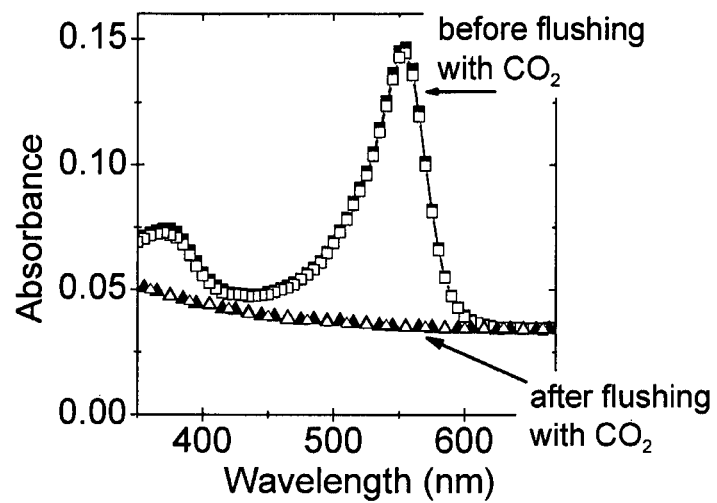
FIG. 1 shows the neutralization of a NaOH solution containing the indicator phenolphthalein with $CO_2$ diffused through a superamphiphobic membrane (indicated by the disappearance of the characteristic absorption of phenolphthalein)

Equation 1:

1. The first example was carried out using a superamphiphobic capillary (length=3 cm, inner diameter=3 mm) and a flow velocity of 7.6 ml/min. The concentration of the sodium hydroxide solution was pH=10.3. UV-VIS spectra were constantly recorded as a function of wavelength (700-350 nm) every 1 min 20 sec (FIG. 1A). Up to 12 min the spectra were constant (only one spectrum shown for clarity). After ~12 min the gas box was flushed with 3-4 liter $CO_2$ (1 balloon) to replace the $N_2$-atmosphere with a $CO_2$-atmosphere. FIG. 1A shows two subsequently recorded spectra: One directly before flushing and the other directly after flushing the gas box with $CO_2$. This diagram demonstrates that the sodium hydroxide solution (pH=10.3) was immediately neutralized and that the main absorption peak of phenolphthalein is no longer detectable.

Figure 1B:
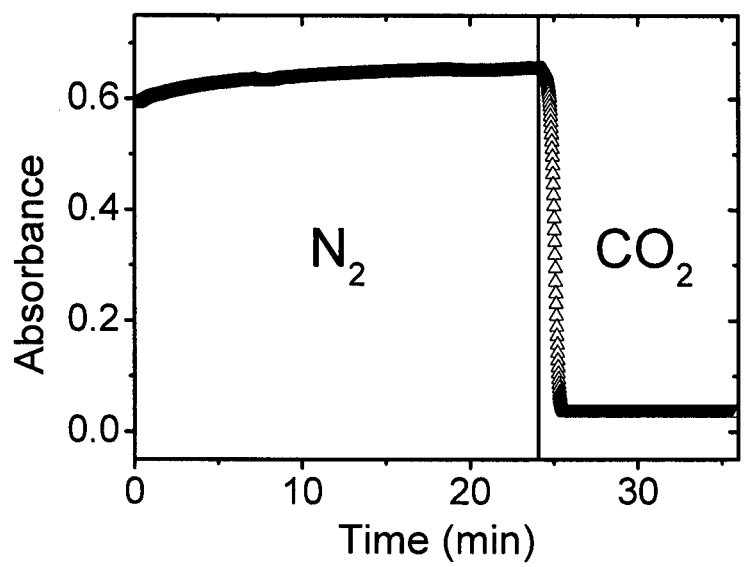

2. The second experiment shows the same principal procedure recorded as a function of time at a constant wavelength (absorption maximum of phenolphthalein at 555 nm) (FIG. 1B). In contrast to the first experiment, the flow cell described in Example 2 was used for this experiment. A sodium hydroxide solution with pH=11.4 was provided and its flow velocity was 7 ml/min. After ~24 min the gas box was flushed with 3-4 liter $CO_2$ (1 balloon) to replace the $N_2$-atmosphere with a $CO_2$-atmosphere.

FIG. 1B shows a significant drop in absorbance after replacing the $N_2$ gas atmosphere of the gas box with 3-4 liter $CO_2$. The absorbance value drops to almost zero what corresponds to a total neutralization of sodium hydroxide in solution due to $CO_2$ diffusion through the superamphiphobic mesh. No liquid leakage could be observed. The timescale of gas-diffusion and neutralization of the actual sodium hydroxide solution passing through the flow cell took roughly about 1 min 12 sec and depends on various points:

Concentration of sodium hydroxide solution

Total Area of interfacial membrane. A=3.1 $cm^2$ for flow cell, A=28 $cm^2$ for capillary Flow speed and flow profile in tube and cuvette Flushing speed/time needed for replacement of $N_2$ by $CO_2$ atmosphere Size of gas chamber (V=~2 liter)

The above experiments demonstrate that gas molecules from the surrounding atmosphere can freely diffuse through these superamphiphobic meshes. The meshes used in said experiments have comparatively big mesh openings (32 micrometers) and the fractal superamphiphobic coating is porous, with pores in the nanometer to micrometer scale. Gas molecules are only a few A in size and, therefore, are able to penetrate the structure easily. Liquid passing through the superamphiphobic capillary or flow cell is repelled and does not penetrate the mesh due to the liquid's surface tension. This allows a continuous pumping of the liquid at a constant flow rate without leakage for several hours.

Example 3

Protein and Cell Adhesion on Superamphiphobic Surfaces

1. Protein Adhesion

Superamphiphobic surfaces prepared as outlined below were brought into contact with human whole blood. After a predetermined time (typically a few hours), the whole blood was removed and the protein adhesion on the surfaces was quantified by the known Pierce Test.

Stainless steel meshes were used for each experiment. The mesh width was 32 micrometers and the steel wires had a diameter of 28 micrometers. Five mesh pieces of 1.5 cm×2.5 cm were cut, rinsed with water, ethanol and water, respectively. One mesh piece was used without any further modification as control.

The other mesh pieces were attached to a steel mounting using a copper wire as shown in FIG. 4C. These suspended mesh pieces were coated with paraffin candle soot from both sides in analogy to the procedure described in Example 1. All steps (CVD of tetraethoxysilane, calcination at 600° C., hydrophobization by CVD of trichlorofluorosilane) were carried out with suspended samples to prevent any possible damage of the coating due to contact with the surrounding environment. Some samples showed manufacturing defects and proved to be hydrophobic but not oleophobic. One of these superhydrophobic but not super-olephobic surfaces was examined as well as a comparative sample (hydrophob, oleophil). For comparison an untreated metal mesh was also investigated (control).

The samples were immerged into whole human blood for 3 days at 21° C. (FIG. 4c). After 3 days the samples were taken out and the upper part, which was not immersed, was cut off.

The resulting meshes (approx. 1.5×1.5 cm) were cut into smaller pieces, weight and transferred to an Eppendorf cup for further protein quantification using the Pierce Test. In principle, the Pierce 660 nm Protein Assay (from Pierce Biotechnology, Rockford, Ill., USA) is a colorimetric method to determine the total protein amount based on absorbance.

Figure 4A:
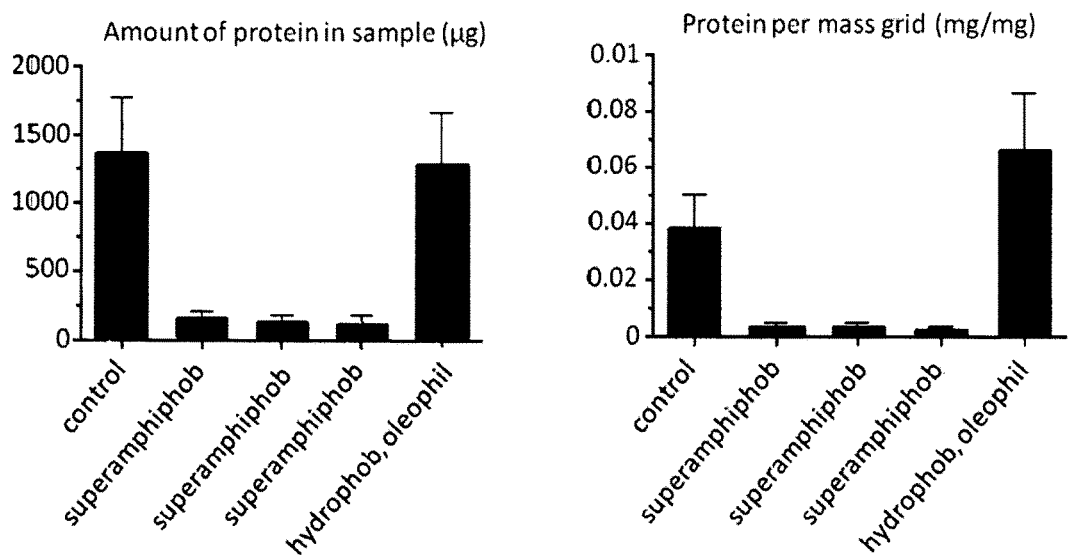

The results of the Pierce Test are shown in FIG. 4A. Results are given in total amount of protein for each sample in microgram (μg) and, since the size of the samples varied slightly, in mass of proteins per milligram (mg) of weight mesh. The values for coated and uncoated meshes can be compared since coated and uncoated meshes are about equal in mass. A significantly reduced protein adhesion could be observed for all three super-amphiphobic meshes (below 0.01 mg protein per mg mesh). The untreated metal mesh showed about 0.04 mg protein per mg mesh and the hydrophob but oleophilic meshes showed about 0.07 mg protein per mg mesh.

2. Cell Adhesion

Superamphiphobic meshes with a size of approx. 1 cm×1 cm were prepared as described above. The samples were introduced into a small sealable chamber with a water reservoir to provide air humidity. Blood drops were put onto the superamphiphobic meshes and the chamber was sealed with parafilm tape. The drops rested statically for 30 min, 4 h 24 min h and 48 h on the meshes and were carefully removed without damaging the surface after the specified times. For comparison, a drop was placed on an uncoated metal mesh. Samples were investigated using scanning electron microscopy.

Figure 4B:
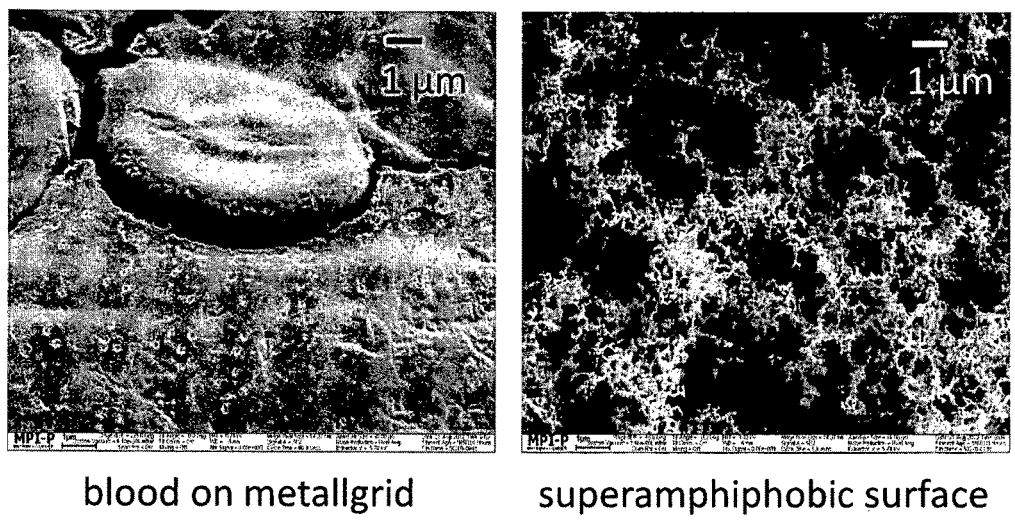

Scanning electron microscopy revealed that the untreated metal mesh was coated with a mixture of cells (6 to 8 micrometers) and an organic residue (FIG. 4B, left). For size comparison, the structure of a superamphiphobic mesh is shown on the right hand side with the same resolution. Even after 48 h incubation time no organic residues could be found on the place where the drop was put using scanning electron microscopy.

The invention claimed is:

1. A method for transferring gas molecules from a gaseous medium into a liquid medium or vice versa comprising at least the following steps:
    a) providing a liquid medium having a surface tension (liquid-air) in a range of from 0.02 N/m to 0.06 N/m,
    b) providing a gaseous medium,
    c) providing a membrane on an interface between the liquid medium and the gaseous medium, wherein the membrane comprises
        i) a carrier substrate with through-going openings having a mean diameter in a range from 0.2 μm to 200 μm, and
        ii) a porous superamphiphobic coating layer with openings having a mean diameter in a range from 0.1 μm to 10 μm, which coating layer comprises a surface exhibiting a contact angle of at least 150° with respect to 10 μl sized drops of water and also a contact angle of at least 150° with respect to 10 μl sized drops of liquids having a surface tension of not more than 0.06 N/m, which is provided at least on a substrate surface facing the liquid medium,
    wherein either the liquid medium or the gaseous medium, comprises at least one target gas to be transferred and said membrane is permeable for the at least one gas to be transferred and not permeable for the liquid medium due to the superamphiphobic properties of the membrane surface facing the liquid medium with respect to said liquid medium,
    d) contacting the gaseous medium with the liquid medium via said superamphiphobic layer for a sufficient time to enrich the liquid or gaseous target medium with the at least one gas to be transferred.

2. The method according to claim 1, wherein gas molecules are transferred from a gaseous medium into a liquid medium.

3. The method according to claim 1, wherein the at least one gas to be transferred is a member selected from the group consisting of oxygen, carbon dioxide, $TiCl_4$, nitrogen oxides, $SO_2$, $SO_3$, $H_2S$, HCl, HCN, ammonia, amines, and silanes.

4. A device for transferring gas molecules and/or particles from a gaseous medium into a liquid medium or vice versa comprising:

a) a liquid medium having a surface tension (liquid-air) in a range of 0.02 N/m to 0.06 N/m,
b) a gaseous medium,
c) a membrane provided on an interface between the liquid medium and the gaseous medium, wherein the membrane comprises
   i) a carrier substrate with through-going openings having a mean diameter in a range from 0.2 µm to 200 µm, and
   ii) a porous superamphiphobic coating layer with openings having a mean diameter in a range from 0.1 µm to 10 µm, which coating layer comprises a surface having a contact angle of at least 150° with respect to 10 µl sized drops of water and also a contact angle of at least 150° with respect to 10 µl sized drops of liquids having a surface tension of not more than 0.06 N/m, which is provided at least on the substrate surface facing the liquid medium,
   which membrane is permeable for at least one gas contained in the liquid or gaseous medium, and not permeable for the liquid medium due to the superamphiphobic properties of the membrane surface facing the liquid medium with respect to said liquid medium.

5. The device according to claim 4 which is a gas scrubber or an oxygenator of a heart-lung machine or a component thereof.

6. The device according to claim 4, wherein the superamphiphobic coating layer comprises strings, particles embedded in fibers, columns, aggregates or an arrangement of nano- or microparticles having a mean diameter in a range of 12 nm to 2 µm, which particles comprise a material of low surface energy or are coated with a material of low surface energy, wherein the low surface energy material has a surface tension (air-substrate surface) less than 0.03 N/m.

7. The device according to claim 4, wherein the carrier substrate comprises a mesh, fibers, a textile, a micro- or mesoporous foam or a porous 3-dimensional structure with a defined shape.

8. The device according to claim 7, wherein the porous 3-dimensional structure with a defined shape comprises an elongated longitudinally extended hollow body having at least one lumen or cavity provided in an interior thereof.

9. The device according to claim 4, wherein the membrane comprises a carrier substrate with a microporous or mesoporous superamphiphobic layer provided on at least one substrate surface and wherein said porous layer is partially filled with the gaseous medium.

10. The device according to claim 4, wherein the liquid medium exerts a hydrostatic pressure of at least 100 Pa, onto the superamphiphobic layer of the membrane.

11. The method according to claim 1, wherein the liquid medium comprises blood, the gaseous medium is oxygen or an oxygen-containing gas mixture and the at least one gas to be transferred from the gaseous medium is oxygen.

12. The device according to claim 4, wherein the membrane is produced by providing a carrier substrate with through-going openings having a mean diameter in a range from 0.2 µm to 200 µm, depositing particles having a mean diameter in a range of from 12 nm to 2 µm on the substrate surface, and, optionally, coating the particles with a hydrophobic top coating.

13. The device according to claim 12, wherein the particles are polymer particles, silica particles or particles coated with a shell selected from the group consisting of a silica shell, a metal oxide shell, a Ti{OCH(CH$_3$)$_2$}$_4$ shell, and a hybrid shell comprising 2 or more materials, wherein the silica particles or particles coated with a shell are further coated with a hydrophobic top coating.

14. The method according to claim 1, wherein the method is used for gas scrubbing, flue gas desulfurization, silane capturing, or for medical treatment.

15. The method according to claim 1, wherein the superamphiphobic coating layer comprises strings, particles embedded in fibers, columns, aggregates or an arrangement of nano- or microparticles having a mean diameter in a range of 12 nm to 2 µm, which particles comprise a material of low surface energy or are coated with a material of low surface energy, wherein the low surface energy material has a surface tension (air-substrate surface) less than 0.03 N/m.

16. The method according to claim 1, wherein the carrier substrate comprises a mesh, fibers, a textile, a micro- or mesoporous foam or a porous 3-dimensional structure with a defined shape.

17. The method according to claim 1, wherein the membrane comprises a carrier substrate with a microporous or mesoporous superamphiphobic layer provided on at least one substrate surface and wherein said porous layer is partially filled with the gaseous medium.

18. The method according to claim 1, wherein the liquid medium exerts a hydrostatic pressure of at least 100 Pa, onto the superamphiphobic layer of the membrane.

19. The method according to claim 1, wherein the membrane is produced by providing a carrier substrate with through-going openings having a mean diameter in a range from 0.2 µm to 200 µm, depositing particles having a mean diameter in a range of from 12 nm to 2 µm on the substrate surface, and, optionally, coating the particles with a hydrophobic top coating.

20. The method according to claim 19, wherein the particles are polymer particles, silica particles or particles coated with a shell selected from the group consisting of a silica shell, a metal oxide shell, a Ti{OCH(CH$_3$)$_2$}$_4$ shell, and a hybrid shell comprising 2 or more materials, wherein the silica particles or particles coated with a shell are further coated with a hydrophobic top coating.

* * * * *